United States Patent
Boit et al.

(10) Patent No.: US 11,350,658 B2
(45) Date of Patent: *Jun. 7, 2022

(54) SUGAR COMPOSITIONS FOR TABLETING BY DIRECT COMPRESSION

(71) Applicant: ROQUETTE FRERES, Lestrem (FR)

(72) Inventors: Baptiste Boit, Locon (FR); Pierre Lanos, La Bassee (FR); Fabrice Buquet, Renescure (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/205,696

(22) Filed: Nov. 30, 2018

(65) Prior Publication Data

US 2019/0090528 A1  Mar. 28, 2019

Related U.S. Application Data

(62) Division of application No. 15/325,030, filed as application No. PCT/IB2015/001302 on Jul. 16, 2015, now abandoned.

(30) Foreign Application Priority Data

Jul. 21, 2014  (EP) ..................................... 14306181

(51) Int. Cl.
| | | |
|---|---|---|
| A23L 33/20 | (2016.01) | |
| A23L 27/30 | (2016.01) | |
| A23L 29/30 | (2016.01) | |
| A23P 10/20 | (2016.01) | |
| A23P 10/25 | (2016.01) | |
| A23P 10/28 | (2016.01) | |
| A61K 31/7004 | (2006.01) | |

(52) U.S. Cl.
CPC ............... *A23L 33/20* (2016.08); *A23L 27/33* (2016.08); *A23L 29/30* (2016.08); *A23P 10/20* (2016.08); *A23P 10/25* (2016.08); *A23P 10/28* (2016.08); *A61K 31/7004* (2013.01); *A23V 2002/00* (2013.01)

(58) Field of Classification Search
CPC .......... A23P 10/20; A23P 10/25; A23P 10/28; A61K 31/7004; A23L 33/20; A23L 27/33; A23L 29/30; A23V 2002/00
See application file for complete search history.

(56) References Cited

U.S. PATENT DOCUMENTS

| | | | |
|---|---|---|---|
| 3,305,447 A | | 2/1967 | Reimers et al. |
| 3,627,583 A | | 12/1971 | Troy et al. |
| 4,698,101 A | * | 10/1987 | Koivurinta ........... A61K 9/2018 127/30 |
| 6,039,813 A | | 3/2000 | Pepper et al. |
| 8,071,558 B2 | † | 12/2011 | Tokuda |
| 2002/0035248 A1 | | 3/2002 | Luhn |
| 2009/0062215 A1 | * | 3/2009 | Tokuda ............... A61K 31/7004 514/25 |
| 2009/0304891 A1 | | 12/2009 | Fujihara et al. |
| 2010/0130435 A1 | † | 5/2010 | Tokuda |
| 2010/0222284 A1 | | 9/2010 | Tokuda et al. |
| 2012/0076908 A1 | | 3/2012 | Fujihara et al. |
| 2012/0259103 A1 | * | 10/2012 | Boit ......................... A23G 4/10 536/18.5 |
| 2012/0329735 A1 | | 12/2012 | Sato et al. |

FOREIGN PATENT DOCUMENTS

| | | |
|---|---|---|
| EP | 1 538 200 A1 | 6/2005 |
| EP | 1 905 442 A1 | 4/2008 |
| EP | 2 156 751 A1 | 2/2010 |
| WO | 2005/060937 A1 | 7/2005 |

OTHER PUBLICATIONS

Jan. 7, 2016 International Search Report issued in International Application No. PCT/IB2015/001302.

* cited by examiner
† cited by third party

*Primary Examiner* — Doan T Phan
(74) *Attorney, Agent, or Firm* — Oliff PLC

(57) ABSTRACT

A directly compressible composition includes more than 30% by weight of allulose. The directly compressible composition can form tablets. A method for the manufacture of allulose granules includes: a step (a) of preparing a granulation liquid comprising allulose; a step (b) of granulating powdery allulose, by applying the granulation liquid obtained in step (a) onto moving powdery allulose; a step (c), simultaneous with step (b), of drying the granules obtained in step (b); a step (c') of maturation of the granules obtained in step (c); and a step (d) of recovering the granules obtained in step (c) or (c').

5 Claims, No Drawings

SUGAR COMPOSITIONS FOR TABLETING BY DIRECT COMPRESSION

The present invention relates to directly compressible compositions comprising more than 30% by weight of allulose, and to tablets obtainable thereof.

PRIOR ART

Allulose is a hexoketose monosaccharide sweetener, which is a C-3 epimer of D-fructose and is rarely found in nature. It has 70% relative sweetness but 0.3% enemy of sucrose, and is suggested as an ideal sucrose substitute for food products. It shows important physiological functions, such as blood glucose suppressive effect, reactive oxygen species scavenging activity, and neuroprotective effect. It also improves the gelling behavior and produces good flavor during food process.

A non-cariogenic sweetener with a major component of allulose has been reported in literature to offer health benefits relevant to weight management and obesity related illnesses (i.e. type it diabetes, metabolic disorders).

Allulose has already been used as a sweetener in food and drink formulations, (see for instance patent applications EP 2 156 751 A1, US 2012/076908 A1 and US 2009/304891 A1), but could not be found in the form of tablets in the prior art.

However there would be a great advantage to have tablets based on allulose, i.e., tablets comprising great amount of allulose, for use as a sweetener with health related benefits in confectionary products as well as nutritional and dietary supplement. Human or vetenary pharmaceutical solid dosage form (tablets) could also take advantages of such excipient.

The direct compression techniques enable the manufacture of tablets containing a precise amount of (active) ingredients, at high speed and at relatively low cost.

Direct compression consists in strongly compressing a powder into a die using a punch, so as to impart thereto the form of a tablet. The high pressure applied allows aggregation of the molecules of the powder which produces a solid tablet.

These powders include various ingredients, usually:

Diluents, also called "direct compression excipients" for the reason that they are the major compounds in the tablets and are responsible for the flow properties and compressibility of the powder to be compressed;

(super-) Disintegrants, whose aim is to facilitate tablet disintegration in aqueous media, to promote the release of active ingredients, for instance when the tablet is ingested;

lubricants, whose role is to enable the ejection of newly formed tablets from their matrices;

glidants, whose role is to promote the flow of the powder within the equipment used for tableting;

pH stabilizing agents, colorants, flavors, surfactants.

Commonly used direct compression excipients are anhydrous lactose, cellulose and microcrystalline cellulose (MCC). Direct compression excipients are the major ingredients in these compositions, as their role and their quantities are of importance in these compositions. They must be in large amounts to allow the obtaining of a solid dosage form. As a result, only a little amount of other material can usually be introduced in tablets. This is why tablets comprising great amounts of allulose could not be found in the prior art.

However, the inventors succeeded in obtaining tablets which can comprise more than 30% by weight of allulose.

To do so, the inventors prepared allulose capable of acting as a direct compression excipient, and as a result, that can be introduced in significant amounts in tablets. The allulose according to the invention can advantageously fill both roles of sweetener and direct compression excipient.

Indeed, allulose is not naturally compressible; meaning that allulose obtained by natural crystallization in water is not compressible. It lacks flow, cohesion or lubricating properties necessary for the production of tablets by direct compression.

The allulose developed by the inventors is in the form of granules, is compressible, and allows the preparation of tablets having hardness greater than 50 N.

There was no hint in the prior art suggesting allulose acting as a direct compression excipient. A fortiori, there was no hint in the prior art suggesting that this allulose needed to be in the form of granules.

OBJECT

It was thus an object of the present invention to provide directly compressible compositions comprising significant amounts of allulose.

It was another object of the invention to provide tablets based on allulose, i.e. tablets exhibiting high amounts of allulose, and at the same time, satisfying hardness.

BRIEF DESCRIPTION OF THE INVENTION

The invention thus first relates to granules of allulose which are compressible in the sole presence of a lubricant, to form a tablet having a diameter of 13 mm, a thickness of 6 mm, an apparent density of 1.35 g/ml±0.02 g/ml, a cylindrical shape with convex faces with a radius of curvature of 13 mm, whose hardness is greater than 50 N.

The present invention also relates to the use of granules of allulose according to the invention as a direct compression excipient in a directly compressible composition.

The present invention also relates to a directly compressible composition comprising the granules of allulose according to the invention.

The present invention also relates to a method for the manufacture of granules of allulose according to the invention, comprising:

a step (a) of preparing a granulation liquid comprising allulose;

a step (b) of granulating powdery allulose, by applying the granulation liquid obtained in step (a) onto moving powdery allulose;

a step (c), preferably simultaneous with step (b), of drying the granules obtained in step (b);

an optional step (c') of maturation of the granules obtained in step (c);

a step (d) of recovering the granules obtained in step (c) or (c').

The present invention further relates to a method for the manufacture of a tablet, comprising the steps of: providing a directly compressible composition according to the invention; followed by directly compressing said composition to form the tablet.

The present invention finally relates to a tablet composed of a directly compressible composition according to the invention, or obtained by the method for the manufacture of a tablet according to the invention.

DETAILED DESCRIPTION OF THE INVENTION

The inventors succeeded in obtaining compositions based on allulose, suitable for direct compression, as evidenced in Example 1. These directly compressible compositions allowed the preparation of tablets having hardness greater than 50 N. They comprised 99% by weight of allulose, and no other direct compression excipient was required to obtain these results.

This allulose was obtained through a process of granulation that can be advantageously carried out by solely using water and allulose.

Granulation refers to the act or process in which primary powder particles are made to bind each other to form multiparticulate agglomerates called granules. It is the process of collecting particles together by creating bonds between them. The two principal types of granulation technologies are wet granulation and dry granulation.

In wet granulation, granules are formed by the addition of a granulation liquid onto a powder bed which is under the influence of an impeller (in a High or Low shear granulator), screws (in a twin screw granulator), a rotating device (for instance a rotating pan or a rotating drum), or even preferably, air (in a fluidized bed granulator or in a spray-drier). The agitation and the wetting of the primary powder along the system results in the aggregation of the particles composing said primary powder to produce wet granules. The granulation liquid is removed by drying. The granulation liquid can be water-based or solvent-based. Typical solvents include water, ethanol and isopropanol either alone or in combination.

The granulation liquid mixed into the powders can form bonds between powder particles that are strong enough to lock them together. However, once the liquid dries, the powders usually fall apart.

Granulation process thus can be very complex depending on the characteristics of the powders, and the final objective.

In general the liquid is not strong enough to create and hold a bond. In such instances, one or more binders are required.

To this end co-processing has been the most widely explored and commercially utilized method for the preparation of granules. It consists in combining through an appropriate process, the material to be granulated with one or more established other excipient, in particular binders.

The one or more binders to be selected will strongly depend on the material to be made compressible, and to the granulation process used. Depending on the method, the one or more binders will be introduced at different time during the process. It can be introduced dissolved in suitable solvent or in the form of a powder that will dissolve in the granulation liquid during the process.

Examples of binders are povidone, microcrystalline cellulose (MCC), carboxymethyl cellulose (CMC), hydroxypropyl cellulose (HPMC), starch derivatives like maltodextrins, acacia gum, tragacanth gum, gelatin.

Povidone, which is a polyvinyl pyrrolidone (PVP), is one of the most commonly used pharmaceutical binders in wet granulation processes. When PVP and a solvent are mixed with powders, PVP forms a bond with the powders during the process, and the solvent evaporates.

Sometimes, the use of a binder is not sufficient, and the powder needs to be pre-treated before to be granulated, typically by undergoing a step of spray-drying.

Surprisingly, and as evidenced in Example 1, the inventors found that the compressible granules of allulose according to the invention could be obtained through particular process of wet granulation, by using allulose itself as a binder.

That is to say, that allulose was turn into granules without the need of being co-processed.

Even more surprisingly, and advantageously, no pre-treatment of the powdery allulose was required to obtain such granules of allulose.

This means that not only the inventors were able for the first time to obtain a directly compressible allulose, but also in doing so, found that this was possible thanks to a particularly easy to carry out process. To be implemented, this process does not require excessive number of materials and of steps.

Moreover the granulation liquid is advantageously water-based, so has the advantage of being safe to deal with.

Thanks to the inventors, it is now possible to obtain tablets, comprising significant amounts of allulose, which can be greater than 30% by weight relative to the total weight of the tablet, typically of between 90 and 99%.

Allulose can advantageously play both role of direct compression excipient and sweetener in the compositions of the present application.

The granules of allulose according to the invention are particularly advantageous for both manufacture of suckable and chewable sweet tablets. Indeed, the tablets obtained out of the granules of allulose according to the invention exhibit excellent taste and texture, as compared to the sweet tablets of prior art, in particular as compared to the tablets made out of directly compressible sweet sugar or sugar alcohol of prior art. These tablets exhibit smooth sensation in the mouth when sucking, with no sticking and no gritty sensation, as well as pleasant chewable texture.

This was not possible before the present invention, because compressible allulose could not be found. If high amounts of allulose would have been used, the compositions obtained thereof would have been impossible to compress.

Granules of allulose according to the invention are compressible in the sole presence of a lubricant, to form a tablet having a diameter of 13 mm, a thickness of 6 mm, an apparent density of 1.35 g/ml±0.02 g/ml, a cylindrical shape with convex faces with a radius of curvature of 13 mm, whose hardness is greater than 50 N, preferably greater than 60 N, preferably greater than 70 N, preferably greater than 80 N, preferably greater than 90 N, preferably greater than 100 N, even more preferably greater than 110 N.

In order to evaluate if a material is compressible and can allow forming tablets having the hardness complying with the invention, the person skilled in the art can adapt the nature and the amount of lubricant used. The material to be compressed can be for instance composed of 99.0% by weight of said material and 1.0% of lubricant, usually magnesium stearate.

The tablet can be formed by means of a single punch press, for instance like the one disclosed in "Procedure 1" hereinafter in the Examples.

The hardness can be evaluated by the person skilled in the art on a hardness tester. An example of such hardness tester is disclosed in "Procedure 1" described hereinafter in the Examples. The value given in newtons usually corresponds to a mean value from 10 measurements.

In general, the hardness is lower than 800 N, even lower than 400 N, even lower than 300 N, even lower than 200 N, even lower than 150 N.

The granules of allulose according to the invention preferably has mean volume diameter D 4.3 between 100 and 1000 µm, preferably between 150 and 800 µm and more preferably between 200 and 500 µm.

The mean volume diameter D 4.3 can be determined by the person skilled in the art on a LASER diffraction granulometer type LS 230 from the company BECKMAN-COULTER, equipped with its powder dispersion module (dry method), following the manufacturers technical manual and specifications. The measurement range of the LASER diffraction granulometer type LS 230 is from 0.04 µm to 2000 µm. The operating conditions of hopper screw speed and intensity of vibration of the dispersion channel are determined in such a way that the optical concentration is between 4% and 12%, ideally 8%. The results are calculated in percentage by volume, and expressed in µm.

Allulose used according to the invention can be in either the D- or L-configuration, however D-allulose is preferred in the present invention, because easier to obtain.

The granules of allulose according to the invention can be used as a direct compression excipient in a directly compressible composition.

In the present invention, "directly compressible composition" means a powdery composition suitable, per se, for the manufacture of tablets by direct compression. This composition always comprises a direct compression excipient or a mixture of direct compression excipients. Such composition allows the manufacture of tablets of sufficient hardness, and of satisfying appearance.

Preferably, the granules of allulose of the invention are further used as a sweetener, preferably as a low-calorie sweetener, i.e. for the manufacture of tablets having calorific value lower than 5 kcal/g, preferably lower than 4 kcal/g, preferably lower than 3 kcal/g, preferably lower than 2 kcal/g, even more preferably lower than 1 kcal/g.

It is preferably used as a sweetener having a relative sweetness, as compared to sucrose, of between 0.5 and 1.0, preferably of between 0.6 and 0.8, typically of 0.7.

Preferably, the granules of allulose of the invention are further used as a health ingredient having physiological functions, such as blood glucose suppressive effect, reactive oxygen species scavenging activity, and/or neuroprotective effect.

It is another object of the present invention to provide a directly compressible composition, comprising the granules of allulose according to the invention.

Thanks to the granules of allulose according to the invention, the directly compressible compositions according to the invention can comprise significant amounts of allulose, notably without requiring the adding of other direct compression excipients.

In the directly compressible composition according to the invention, granules of allulose preferably represent at least 30% of the directly compressible composition, preferably at least 40%, preferably at least 50%, preferably at least 60%, preferably at least 70%, preferably at least 80%, preferably at least 90%, typically between 90 and 99%, even between 95 and 99%, said percentage being expressed in dry weight, with respect to the total dry weight of said directly compressible composition.

Preferably, the directly compressible compositions according to the invention comprises no more than 60% of direct compression excipients other than the granules of allulose according to the invention, preferably no more than 50%, no more than 40%, preferably no more than 30%, preferably no more than 20%, preferably no more than 10%, preferably no more than 5%, more preferably no more than 2%, and most preferably 0%, said percentage being expressed in dry weight, with respect to the total dry weight of said directly compressible composition.

It is another object of the present invention to provide a method for the manufacture of granules of allulose according to the invention, comprising:
 a step (a) of preparing a granulation liquid comprising allulose;
 a step (b) of granulating powdery allulose, by applying the granulation liquid obtained in step (a) onto moving powdery allulose;
 a step (c), preferably simultaneous with step (b), of drying the granules obtained in step (b);
 an optional step (c') of maturation of the granules obtained in step (c);
 a step (d) of recovering the granules obtained in step (c) or (c').

In general, step (a) simply consists in dissolving powdery allulose into water, to obtain an aqueous solution of allulose.

Powdery allulose can be, for instance, individual crystals, classically obtained by crystallization from a solvent such as water or a mixture of water and ethanol, preferably water alone.

Powdery allulose can also be composed of, or can also comprise, the granules obtained in step (c) or (c'), which are preferably grinded before undergoing step (b).

Step (a) is preferably performed at a temperature which allows good dissolving of allulose into water. It is preferably performed at ambient temperature as allulose is very soluble in water (about 225 g per 100 ml water at 20° C.). For the preparation of a granulation liquid comprising higher concentrations of allulose, a heating will be required. Typically the allulose will be dissolved in water heated from 85° C. to 100° C.

Preferably, the granulation liquid is applied by means of a spraying system, for instance by using one or more spraying nozzle(s). It is preferably applied in the form of fine droplets.

The quality of the contact between the granulation liquid and the powdery allulose during step (b) notably depends on the mean used to move the powdery allulose. This can be performed by subjecting the powder to the influence of an impeller (in a High or Low shear granulator), screws (in a twin screw granulator), a rotating device (for instance a rotating pan or a rotating drum), or even preferably, air (in a fluidized bed granulator or in a spray-drier).

The drying performed in step (c) is preferably performed concomitantly to the granulation step (b), by way of a granulator using air for granulation and for drying like spray-driers or fluidized bed granulators and dryers.

The method for the manufacture of granules of allulose according to the invention is preferably a continuous process using in particular a mixer-granulator, a continuous fluid bed granulator, or a spray-dryer.

The continuous process preferably includes the recycling of the granules obtained in step (c) or (c'). In this case, the granules are preferably grinded before undergoing step (b). The amount of recycled granules can be adapted so as to optimize the crystallization of allulose, to prevent the excessive formation of amorphous allulose. The ratio by weight of granulation liquid to the recycled granules is thus preferably of between 1:2 and 1:15, preferably of between 1:4 and 1:10.

The continuous process can be performed in an spray-dryer preferably equipped with a high pressure spray-drying nozzle, for instance of MSD-type, which preferably comprises the recycling of particles in the drying chamber.

Granulation may be carried out using, for example, a mixer-granulator operating batchwise, semi-continuously or continuously such as the vertical FLEXOMIX marketed by SCHUGI, a device of the DRIAM or DUMOULIN type, or the horizontal CB marketed by LÖDIGE into which is introduced, by way of a weight feeder, the starting powdery allulose to be granulated continuously and the granulation liquid by way of a volumetric feeder.

When using a SCHUGI vertical FLEXOMIX type, the starting powdery allulose and the granulation solution are very intimately mixed in the mixer-granulator fitted with a shaft with knives arranged in the form of blades, and a system of spraying liquids by way of injection nozzles.

According to a preferred embodiment of the invention, satisfactory dispersion of the constituents and agglomeration of the particles of the starting powdery allulose are carried out by high speed stirring, i.e. at a value at least equal to 1000 rpm, preferably at least equal to 3500 rpm. At the outlet of the mixer-granulator, the granules formed are discharged continuously into a dryer-ageing device.

Discharge takes place preferably by gravity in the case of said vertical granulator, and by thrust by way of the shaft of rotating knives if the horizontal granulator is used.

This second drying-ageing step at the outlet of the mixer-granulator makes it possible to remove, if necessary, all or part of the water originating from the binder such that crystallization and stabilization take place after the prior granulation step.

The dryer-ageing device may be, for example, a fluidized bed dryer-ageing device or a rotary ageing drum. The allulose according to the invention is obtained after cooling and optionally sieving.

In this case, the fine particles may be recycled directly to the start of granulation, and the coarse particles may be ground and recycled to the start of sieving.

Granulation can be performed in a high shear granulator, using a high speed propeller and a chopper to avoid too big lumps to be created. Such high shear granulators are very common in the pharmaceutical industry and manufactured by well-known suppliers (GLATT, DIOSNA, IMA and the like). Using such equipment the drying step (c) has to be done after the granulation step (b).

On the opposite, fluidized bed granulators (GLATT, GEA and the like) enable to do granulation step (b) and drying step (c) concomitantly. This process used to be a batch one but modern fluid bed granulators have been designed to run continuously. Such continuous equipment is preferred.

For step (a), and because this is more convenient, the starting allulose is in general the same as the one used in the moving powdery allulose.

Optional step (c') can be performed to allow granules to further crystallization and stabilization at a controlled temperature. This step (c') is preferably performed in a fluid bed or in a rotary drum.

The granules of allulose according to the invention may comprise other ingredients, as long as it does not negatively affect the desired properties of the granules.

When present, the other ingredients are generally introduced in the process of manufacture of granules of allulose according to the invention, via the granulation liquid or via the moving powdery allulose.

Such 'other ingredients' can be without limitation:
binders such as polyvinyl pyrrolidone, CMC, HPMC, cellulosic derivatives, acacia gum, gelatin, starch derivatives like maltodextrins, tragacanth gum and the like;
food additives, colorants, glidants, lubricants, pharmaceutical, nutraceutical or veterinary active ingredients, preservatives, stabilizing ingredients;
or mixtures thereof.

However, to limit the number of materials used, and because it is not required to obtain a satisfactory direct compression excipient, the granules preferably contain substantially no binders, other than allulose.

In general, the total amount of 'other ingredients', will be lower than 80%, preferably lower than 40%, preferably lower than 10%, preferably lower than 5%, most preferably equal to 0%, said percentage being expressed in dry weight, with respect to the total dry weight of said granules.

By 'other ingredients' the inventors do not mean to include impurities, like those resulting from the synthesis of allulose, typically residual fructose.

In particular, the allulose such as defined in the present invention generally has purity between 95.0 and 99.9%, said percentage being expressed in dry weight of allulose with respect to the total dry weight of said allulose The purity can in particular be determined by the person skilled in the art by using HPLC method with calcium column.

It is another object of the present invention to provide a method for the manufacture of a tablet, comprising the steps of: providing a directly compressible composition according to the invention; followed by directly compressing the composition to form the tablet.

It is another object of the present invention to provide a tablet, composed of the directly compressible composition according to the invention.

In the present invention, "tablet" means any solid edible preparation, which is obtained by direct compression. These tablets can be in the form of suckable tablets like mints, or in the form of soft or hard chewable tablets. They can be normal or multi layers tablets. They can be used as a nutritional or dietary supplement, or as a pharmaceutical, and can be intended for humans, adults or children, or to animals. Preferably the tablet is a sweet tablet, having calorific value lower than 5 kcal/g, preferably lower than 4 kcal/g, preferably lower than 3 kcal/g, preferably lower than 2 kcal/g, even more preferably lower than 1 kcal/g.

It preferably has a relative sweetness, as compared to sucrose, of between 0.5 and 1.0, preferably of between 0.6 and 0.8, for example of 0.7.

Preferably, the tablet according to the invention has hardness greater than 50 N, preferably greater than 60 N, preferably greater than 70 N, preferably greater than 80 N, preferably greater than 90 N, preferably greater than 100 N, preferably greater than 110 N.

In general, the hardness of the tablet is lower than 800 N, even lower than 700 N, even lower than 600 N, even lower than 500 N, even lower than 400 N, even lower than 300 N, even lower than 200 N, even lower than 150 N.

The tablets according to the invention can be coated, notably by regular spray-drying of a film-forming composition onto a moving bed of tablets. The coating layer in general, will not exceed 5% in weight of the coated tablet. The tablets may also be coated with sugars or polyols, using a "sugar-coating" process to form a frosting or a soft or hard coating, depending on the amount of powders or the coating process used.

The directly compressible compositions and the tablets according to the invention generally comprise other ingredients. Such 'other ingredients' can be without limitation:
direct compression excipient other than allulose, for example (i) directly compressible sugar alcohols like directly compressible forms of sorbitol, mannitol, maltitol, xylitol, isomalt, lactitol, erythritol, (ii) directly compressible sugars like directly compressible forms of sucrose, dextrose, dextrates, lactose, (iii) microcrystalline cellulose, (iv) directly compressible minerals; however it is reminded that the composition for tableting by direct compression according to the present invention preferably comprises no more than 60%, and most preferably 0% of direct compression excipient other than allulose;

dispersants or disintegrants, for example sodium starch glycolate, crosslinked carboxymethyl cellulose, crosslinked polyvinylpyrrolidone, starches;

granulating agents such as polyvinyl pyrrolidone, acacia gum, dextrose, gelatin, maltodextrin, starch and starch derivatives, tragacanth gum and the like;

lubricants, for example magnesium stearate, stearic acid, sodium stearyl fumarate, sucroesters;

food additives, such as flavoring agents, for instance mint, honey, essential oils such as citrus, peppermint or eucalyptus, fruit flavors, acidulants such as citric acid, acidity regulators;

colorants like mineral dyes, pigments or solubles colorants;

glidants (for example silica dioxide) or ant sticking agent (for example talcum);

pharmaceutical, nutraceutical or veterinary active substances;

and mixtures thereof.

The following Examples serve to illustrate the invention and should by no means be construed so as to limit the scope of the invention.

EXAMPLES

In the following examples, granules of allulose according to the invention were prepared and put into the form of tablets whose hardness was determined, according to the Procedure 1 described below.

An allulose of prior art, obtained by crystallization in water, was used for comparison.

Procedure 1—Tablets Preparation and Hardness Measurement

Compositions composed of 99.0% by weight of the material to be tested as a direct compression excipient and 1.0% by weight of magnesium stearate were first prepared.

Tablets were prepared out from these compositions, by means of the single punch laboratory press FROGERAIS AM (SVIAC, Anthony, France).

These tablets had a diameter of 13 mm, a thickness of 6 mm, an apparent density of 1.35 g/ml±0.02 g/ml, and a cylindrical shape with convex faces with a radius of curvature of 13 mm.

The inventors measured the hardness of the tablets thus obtained on an ERWEKA TBH 30 GMD hardness tester (ERWEKA, Heusenstamm, Germany). The value given in Newtons corresponds to a mean value from 10 measurements.

Example 1—Preparation of Granules of Allulose According to the Invention Using a Batch Fluid Bed Granulator Granules of allulose were prepared in a fluid bed granulator Strea-1 (Aeromatic_Fielder/GEA—Bubendorf Switzerland). A solution of allulose is prepared by dissolving 25 g of allulose in 125 ml of water. This solution is sprayed on 300 g of powdery allulose fluidized in the fluid bed granulator. The allulose powder used has a mean diameter of 85 µm. The fluidizing air entrance is at 60° C. and the outlet air at 35° C. This solution is added during 15 minutes (spraying speed about 10 ml per minute). The drying (air at 60° C.) is pursued about 30 minutes after the end of the spraying so that the powder is sufficiently dried. The granules obtained are sieved between 100 µm and 1000 µm to remove the fine and coarse particles, to give granules [i-A].

Example 2—Preparation of Granules of Allulose According to the Invention Using a Rotating Pan Granulator Allulose granules were prepared using home-made rotating pan granulator. An allulose solution was prepared by dissolving 450 g of allulose crystal in 50 g water at a temperature of 85 to 100° C. The solution was sprayed, with compressed air nozzle, on allulose dry powder in a rotating pan with a ratio of liquid to powder at 1:4. The liquid spray rate was about 7.5 ml per minute. The liquid temperature was maintained at 90° C. during the process. Granules of allulose of a few millimeters were formed and continuously discharged out of rotating pan while the volume in the pan remains at constant. The granules were dried and maturated at forced-air circulation oven at 75° C. for 2 hours and conditioned at ambient temperature for 4 hours. The granules were then grinded and sieved at desired particle size of between 100 and 1000 µm to give granules [i-B].

The granules of allulose [i-A] and [i-B] thus obtained were evaluated in compositions for tableting by direct compression, and compared with allulose of prior art obtained by crystallization in water (allulose [c-C]).

To this end, tablets were prepared out of these materials, the hardness of which was evaluated according to "Procedure 1". Results are showed in Table 1.

TABLE 1

Comparison of the properties of granules of allulose according to the invention with allulose of prior art

| | Hardness according to "Procedure 1" |
|---|---|
| [i-A] | 91N |
| [i-B] | 112N |
| [c-C] | Not compressible |

These results show that the inventors succeeded for the first time in obtaining a composition comprising high amounts of allulose, which is compressible.

The inventors succeeded for the first time in obtaining directly compressible allulose, allowing the preparation of tablets having hardness greater than 50 N, in the sole presence of a lubricant, in particular in the present case, from compositions composed of 99.0% by weight of granules of allulose according to the invention and 1.0% by weight of magnesium stearate.

The tablets thus obtained exhibited excellent taste and texture. They showed particularly smooth sensation in the mouth when sucking, with no sticking and no gritty sensation, as well as particularly pleasant chewable texture.

What is claimed is:
1. A method of preparing a direct compression excipient in a directly compressible composition by providing an effective amount of allulose granules as the excipient,
wherein said allulose granules are obtained according to a method comprising:
step (a) of preparing a granulation liquid consisting of allulose and water;

step (b) of granulating powdery allulose, by applying the granulation liquid obtained in step (a) onto moving powdery allulose to obtain allulose granules;

step (c), simultaneous with step (b), of drying the allulose granules obtained in step (b);

step (c') of maturation of the allulose granules obtained in step (c); and step (d) of recovering the allulose granules obtained in step (c) or (c'); and wherein said allulose granules contain no binders other than allulose.

2. The method according to claim 1, wherein said allulose granules are compressible in the sole presence of a lubricant to form a tablet having a diameter of 13 mm, a thickness of 6 mm, an apparent density of 1.35 g/ml±0.02 g/ml, a cylindrical shape with convex faces with a radius of curvature of 13 mm, and a hardness of greater than 50 N.

3. The method according to claim 1, wherein the allulose granules are further used as a sweetener, a low-calorie sweetener, a health ingredient having physiological functions, or combination thereof.

4. A method of preparing allulose granules, comprising:

step (a) of preparing a granulation liquid consisting of allulose and water;

step (b) of granulating powdery allulose, by applying the granulation liquid obtained in step (a) onto moving powdery allulose to obtain allulose granules;

step (c), simultaneous with step (b), of drying the allulose granules obtained in step (b);

step (c') of maturation of the allulose granules obtained in step (c); and step (d) of recovering the allulose granules obtained in step (c) or (c'), wherein said allulose granules contain no binders other than allulose.

5. The method according to claim 4, wherein said allulose granules are compressible in the sole presence of a lubricant to form a tablet having a diameter of 13 mm, a thickness of 6 mm, an apparent density of 1.35 g/ml±0.02 g/ml, a cylindrical shape with convex faces with a radius of curvature of 13 mm, and a hardness of greater than 50 N.

* * * * *